(12) United States Patent
Beretta

(10) Patent No.: US 8,067,152 B2
(45) Date of Patent: Nov. 29, 2011

(54) LIVER CANCER BIOMARKERS

(75) Inventor: Laura Beretta, Mercer Island, WA (US)

(73) Assignee: The Fred Hutchinson Cancer Research Center, Seattle, WA (US)

(*) Notice: Subject to any disclaimer, the term of this patent is extended or adjusted under 35 U.S.C. 154(b) by 716 days.

(21) Appl. No.: 11/708,202

(22) Filed: Feb. 20, 2007

(65) Prior Publication Data

US 2007/0202496 A1 Aug. 30, 2007

Related U.S. Application Data

(60) Provisional application No. 60/777,087, filed on Feb. 27, 2006.

(51) Int. Cl.
  *C12Q 1/00* (2006.01)
  *G01N 33/53* (2006.01)
  *G01N 33/574* (2006.01)

(52) U.S. Cl. ............ 435/4; 435/7.1; 435/7.21; 435/7.23

(58) Field of Classification Search ........................ None
See application file for complete search history.

(56) References Cited

U.S. PATENT DOCUMENTS

| | | | |
|---|---|---|---|
| 7,387,881 B2 * | 6/2008 | Hanash et al. | 435/7.23 |
| 2002/0052308 A1 * | 5/2002 | Rosen et al. | 514/1 |
| 2002/0115094 A1 | 8/2002 | Farnham et al. | |
| 2003/0108553 A1 * | 6/2003 | Hanash et al. | 424/155.1 |

OTHER PUBLICATIONS

Denning et al. (Blood, 1997, 90:372-381).*
Boyd (The Basic Science of Oncology, 1992, McGraw-Hill, Inc., p. 379).*
Lebert et al. (Cancer. Sep. 1, 2003; 98(5):970-7).*
Glaessgen et al. (APMIS 2008 116: 888-95).*
Tockman et al (Cancer Res., 1992, 52:2711s-2718s).*
Kim et al. (Electrophoresis, 2002, 23:4142-4156).*
ERp57 (N-20): sc-18619 (Santa Cruz Biotechnology, Inc., 2006).*
Erp57 (Grp58) Monoclonal Antibody (Map.Erp57) (Assay Designs/Stressgen® Jun. 11, 2008).*
Tang, Z-Y. (Surgical Treatment: Evidence-Based and Problem Oriented, Multimodality treatment for hepatocellular carcinoma, Holzheimer and Mannick, eds. 2001, NCBI Bookshelf).*
Le Naor, F, et al., A Distinct Repertoire of Autoantibodies in Hepatocellular Carcinoma Identified by Proteomic Analysis, Molecular & Cellular Proteomics (2002) 197-203, 1:3.
Hong, S-H, et al., An Autoantibody-Mediated Immune Response to Calreticulin Isoforms in Pancreatic Cancer, Cancer Research (Aug. 1, 2004) 5504-5510, 64.

* cited by examiner

*Primary Examiner* — Peter J Reddig
(74) *Attorney, Agent, or Firm* — Myers Bigel Sibley & Sajovec, P.A.

(57) ABSTRACT

A method of detecting whether a subject is afflicted with or at increased risk of developing liver cancer is carried out by detecting cleavage of a marker in a sample such as a blood sample from the subject. Suitable markers include but are not limited to, calreticulin, calreticulin precursor, protein disulfide isomerase family A member 3 (PDIA3), and cleavage products thereof. The cleavage, or extent of cleavage, can be as compared to that found in a control sample.

24 Claims, 7 Drawing Sheets

2-D pattern of human liver proteins.

Subcellular localization of identified proteins.

2-D pattern of calreticulin isoforms in tumor tissue.

Analysis of calreticulin isoforms.

Analysis of PDIA3 isoforms.

Analysis of GRP78 isoforms.

Analysis of PDI isoform.

Measurement by ELISA of calreticulin and PDIA3 fragments in sera.

ROC curves comparing calreticulin, PDIA3 and AFP individually or in combination in patients with HCC versus those with cirrhosis.

US 8,067,152 B2

LIVER CANCER BIOMARKERS

CROSS-REFERENCE TO RELATED APPLICATION

This application claims the benefit of provisional application Ser. No. 60/777,087, filed Feb. 27, 2006, the disclosure of which is hereby incorporated herein by reference in its entirety.

GOVERNMENT FUNDING

This invention was made with government support under grant numbers CA084986 and DK066840 awarded by the National Institutes of Health. The government has certain rights to this invention.

FIELD OF THE INVENTION

The present invention concerns methods of screening for or detecting liver cancer in subjects, including subjects with or without previously detected risk factors for liver cancer.

BACKGROUND OF THE INVENTION

Hepatocellular carcinoma (HCC), the major histological form of primary liver cancer, affects approximately half a million persons each year, making it the fifth most common malignancy and the third most common cause of cancer death worldwide.[1] The etiology of HCC is mainly associated with hepatitis B virus (HBV) or hepatitis C virus (HCV) chronic infection.[2] In the past decade, there has been a rising incidence of HCC and a progressive increase in HCC-related mortality in the United States and Western Europe.[3,4] The similarity between incidence and mortality rates is indicative of the rapid death after diagnosis in most cases of HCC, with a 5-year survival rate of less than 5%.[3] The poor survival of patients with HCC is largely related to the lack of reliable tools for early diagnosis. At-risk patients with chronic viral hepatitis and cirrhosis are routinely screened for HCC with annual serum alpha-fetoprotein (AFP) and ultrasonography (for healthy hepatitis B virus carriers) or with twice-yearly serum AFP and ultrasonography (for patients with cirrhosis of any etiology).[5] However, the usefulness of AFP as a marker has been overshadowed by its inability to diagnose early-stage tumors efficiently;[6,7] AFP levels may increase transiently, intermittently, or permanently in patients with viral hepatitis without HCC. The lack of efficiency of AFP as a serum marker for HCC surveillance or diagnosis has led to assessment of other serological markers such as alpha-1-antitrypsin,[8] des-gamma-carboxyprothrombin,[9,10] glycipan-3,[11] or isoenzymes of gamma-glutamyltransferase.[12,13]

SUMMARY OF THE INVENTION

A method of screening for or detecting liver cancer in a subject, comprises (a) collecting a sample from the subject; and then (b) detecting an altered level of a liver cancer marker in the sample, an altered level of said marker indicating the subject is afflicted with or at risk of developing liver cancer.

The present invention provides a method of screening for or detecting liver cancer in a subject. The method may be carried out on a sample such as a blood or tissue sample collected from the subject.

In general, the method is carried out by detecting cleavage of a marker in that sample, with cleavage of the marker indicating the subject is afflicted with, or at risk of developing, liver cancer. Suitable markers include but are not limited to, calreticulin, calreticulin precursor, protein disulfide isomerase family A member 3 (PDIA3), and cleavage products thereof. The cleavage, or extent of cleavage, can be as compared to that found in a control sample. Such a control sample may be taken from the same subject at a different (e.g., earlier) point in time or from a different subject or population of subjects considered to be free of, or at no more than normal risk of, liver cancer.

A second aspect of the invention is the use of a means of detecting cleavage of a marker as described herein for carrying out a method of detecting affliction with, or risk of developing, liver cancer as described herein.

The foregoing and other objects and aspects of the present invention are explained in greater detail in the drawings herein and the specification set forth below.

DETAILED DESCRIPTION OF THE PREFERRED EMBODIMENTS

1. Definitions

Figure 1:
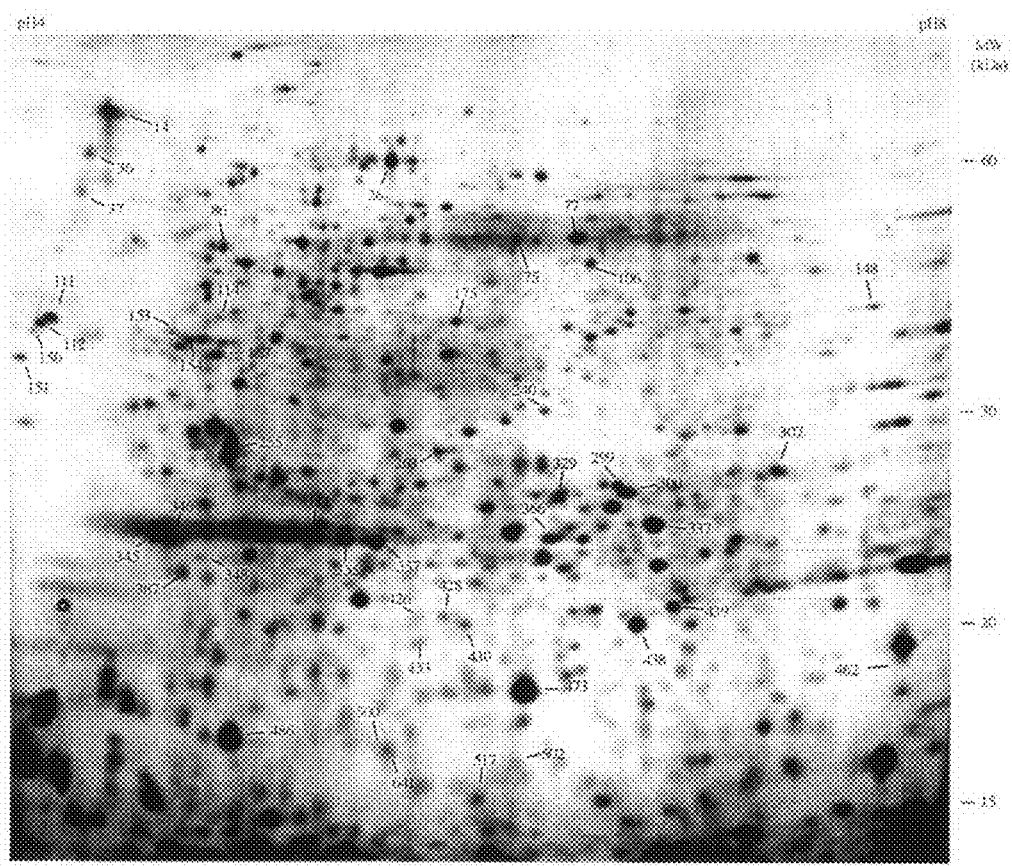
FIG. 1. 2-D pattern of human liver proteins. Two hundred micrograms of proteins were separated in the first dimension by isoelectric focusing. Separation in the second dimension was performed using an acrylamide gradient (11 to 14%) followed by silver staining. The 47 spots identified by computer-assisted analysis as being disregulated in HCC are labeled according to Table 1.

"Altered level" as used with respect to marker proteins herein refers to an increased level (e.g., a one or two fold increase, or more) or a decreased level (e.g., a one or two-fold decrease, or more) in the quantity of marker protein detectable in or via a biological sample from a subject, as compared to a level of marker protein in a corresponding subject not afflicted with a liver disease such as liver cancer.

"Biological sample" as used herein refers to any material taken from the body of a subject which carries the target compound or compounds of the tests described herein, including both tissue samples and biological fluids such as blood samples, saliva samples, urine samples, etc.

"Blood sample" as used herein refers to whole blood or any fraction thereof that contains detectable levels of marker proteins therein (if marker proteins are present in the whole blood sample from which said fraction is obtained), and in particular embodiments refers to a blood sera or blood plasma sample.

"Detecting" or "screening" as used herein means providing an indication that a subject is afflicted with or at risk of developing a disease, particularly a liver disease such as liver cancer, and includes other terms such as screening for a disease, providing a risk assessment for disease, prognosing disease, diagnosing disease, etc. It will be appreciated that no such technique is perfect and that such diagnosis, prognosis or the like may be confirmed by other procedures such as physical examination, imaging, histological examination of tissue samples, etc.

"Isoform" as used herein refers to a different form of a protein, regardless of whether it originates from a different gene or splice variant or by modification of a single gene product. Thus "isoform" as used herein refers to a form of a protein that migrates differently from another form of that protein on a 2 dimensional gel.

"Marker protein" as used herein refers to any protein which can be detected, directly or indirectly (e.g., via an analog, metabolite, fragment or breakdown product) in a biological sample from a subject, an increase or decrease of the amount of which, compared to amounts found in similar subjects without disease, is indicative of the presence or risk of liver cancer in a subject. Marker proteins described herein include any protein listed in Table 1-2 herein. The analog, metabolite, fragment or breakdown product of the marker protein may or may not possess the functional activity of the marker protein.

"Additional liver cancer marker" as used herein can be an elevation (or decrease) in a patient sample of alpha fetoprotein, des-carboy-prothrombin (DCP), carcinoembryonic antigen (CEA), a marker as described in Farnham and Braveel, US Patent Application No. US 2002/0115094, an additional marker as described in Tables 1-2 herein, or any other liver cancer marker.

"Liver cancer" as used herein includes any type of liver cancer, such as those arising from hepatocytes (hepatomas or hepatocellular carcinomas), as well as fibrolamellar hepatomas and cholangiocarcinomas (or bile duct cancer).

"Subjects" as described herein are generally human subjects and includes "patients". The subjects may be male or female and may be of any race or ethnicity, including but not limited to Caucasian, African American, African, Asian, Indian, etc. The subjects may be of any age, including newborn, neonate, infant, child, adolescent, adult, and geriatric. Subjects may also include animal subjects, particularly mammalian subjects such as dog, cat, horse, mouse, rat, etc., screened for veterinary medicine or pharmaceutical drug development purposes.

Subjects include but are not limited to those who have, possess, have been exposed to, or have been previously diagnosed as afflicted with one or more risk factors for liver cancer, including but not limited to: subjects afflicted with or suspected of being afflicted with cirrhosis (e.g., caused by excessive alcohol consumption), subjects afflicted with, infected with, or suspected of being exposed to or infected with hepatitis B or hepatitis C virus, subjects afflicted with or suspected of being afflicted with haemochromatosis, and subjects who have consumed, or are suspected of having consumed, a toxin such as aflatoxin (e.g., found in moldy foods such as grain, peanuts, etc.).

The disclosures of all United States patent references cited herein are to be incorporated herein by reference in their entirety.

While the following description focuses primarily on liver cancer, it will be appreciated that the present invention may also be utilized in connection with other liver diseases as noted above.

2. Assay Procedures

The step of collecting a sample such as a blood sample from a subject can be carried out by phlebotomy or any other suitable technique, with the blood sample processed further to provide a serum sample or other suitable blood fraction. The step of determining the presence of an altered level of a marker protein in the sample, and/or depressed level of a marker protein in the sample, can also be carried out in accordance with known techniques, including but not limited to mass spectrometry, chromatography, electrophoresis, sedimentation, isoelectric focusing, and antibody assay. See, e.g., U.S. Pat. No. 6,589,748; U.S. Pat. No. 6,027,896. Marker proteins may also be identified by two-dimensional electrophoresis (2-D electrophoresis). 2D-electrophoresis is a technique comprising denaturing electrophoresis, followed by isoelectric focusing; this generates a two-dimensional gel (2D gel) containing a plurality of separated proteins. For an example of a preferred means of carrying out 2D-electrophoresis to identify marker proteins, see, e.g. WO 98/23950; U.S. Pat. No. 6,064,654 and U.S. Pat. No. 6,278,794. Briefly, spots identified in a 2D gel are characterized by their isoelectric point (pI) and apparent molecular weight (MW) as determined by 2D gel electrophoresis. Altered levels of marker proteins in a first sample or sample set with respect to a second sample or sample set can be determined when 2D gel electrophoresis gives a different signal when applied to the first sample and second samples or sample sets. Altered levels of marker proteins may be present in first sample or sample sets at increased, elevated, depressed or reduced levels as compared to the second sample or sample sets. By "increased level" is meant (a) any level of a particular isoform of marker protein when that isoform is not present in a normal subject without liver cancer, as well as (b) an elevated level (e.g., a two or three-fold increase) of marker protein or a particular isoform of a marker protein when that protein or a particular isoform is present in a normal subject without liver cancer. By "depressed level" is meant (a) an absence of a particular isoform of a marker protein when that isoform is present in a normal subject without liver cancer, as well as (b) a reduced level (e.g., a two or three-fold reduction) of a marker protein or a particular isoform of a marker protein when that protein or a particular isoform is present in a normal subject without liver cancer. In general, the steps of (a) assaying a sample for an elevated level of a marker protein and/or depressed level of a marker protein, and (b) correlating an elevated level of a marker protein and/or a depressed level of a marker protein in said sample with liver cancer, can be carried out in accordance with known techniques, or variations thereof that will be apparent to persons skilled in the art. See, e.g., U.S. Pat. No. 4,940,658 to Allen et al.

Signals obtained upon analyzing a biological sample or sample set from subjects having liver cancer relative to signals obtained upon analyzing a biological sample or sample set from normal subjects without liver cancer will depend upon the particular analytical protocol and detection technique that is used. Accordingly, the invention contemplates that each laboratory will establish a reference range for each marker protein identifier (e.g. pI and/or MW) in normal subjects without liver cancer according to the analytical protocol and detection technique in use, as is conventional in the diagnostic art.

Antibody assays (immunoassays) may, in general, be homogeneous assays or heterogeneous assays. In a homogeneous assay the immunological reaction usually involves the specific antibody, a labeled analyte, and the sample of interest. The signal arising from the label is modified, directly or indirectly, upon the binding of the antibody to the labeled analyte. Both the immunological reaction and detection of the extent thereof are carried out in a homogeneous solution. Immunochemical labels which may be employed include free radicals, radioisotopes, fluorescent dyes, enzymes, bacteriophages, coenzymes, and so forth.

In a heterogeneous assay approach, the reagents are usually the specimen, the antibody of the invention and a system or means for producing a detectable signal. Similar specimens as described above may be used. The antibody is generally immobilized on a support, such as a bead, plate or slide, and contacted with the specimen suspected of containing the antigen in a liquid phase. The support is then separated from the liquid phase and either the support phase or the liquid phase is examined for a detectable signal employing means for producing such signal. The signal is related to the presence of the analyte in the specimen. Means for producing a detectable signal include the use of radioactive labels, fluorescent labels, enzyme labels, and so forth. For example, if the antigen to be detected contains a second binding site, an antibody which binds to that site can be conjugated to a detectable group and added to the liquid phase reaction solution before the separation step. The presence of the detectable group on the solid support indicates the presence of the antigen in the test sample. Examples of suitable immunoassays are the radioimmunoassay, immunofluorescence methods, enzyme-linked immunoassays, and the like.

Those skilled in the art will be familiar with numerous specific immunoassay formats and variations thereof which may be useful for carrying out the method disclosed herein. See generally E. Maggio, Enzyme-Immunoassay, (1980) (CRC Press, Inc., Boca Raton, Fla.); see also U.S. Pat. No. 4,727,022 to Skold et al. titled "Methods for Modulating Ligand-Receptor Interactions and their Application," U.S. Pat. No. 4,659,678 to Forrest et al., U.S. Pat. No. 4,316,110 to David et al., U.S. Pat. No. 4,275,149 to Litman et al., U.S. Pat. No. 4,233,402 to Maggio et al., and U.S. Pat. No. 4,230,767 to Boguslaski et al.

Antibodies for immunoassays can be polyclonal or monoclonal antibodies, Fab fragments, humanized antibodies and chimeric antibodies (including fragments thereof) and can be produced in accordance with known techniques, based on one or more marker protein. For example, monoclonal antibodies may be produced in a hybridoma cell line according to the techniques of Kohler and Milstein, *Nature* 265, 495-97 (1975). Monoclonal Fab fragments may be produced in *Escherichia coli* from the known sequences by recombinant techniques known to those skilled in the art. See, e.g., W. Huse, *Science* 246, 1275-81 (1989) (recombinant Fab techniques). Polyclonal antibodies can be produced in animals such as goats, rabbits and horses by administration of one or more marker protein, optionally in combination with an adjuvant, as an immunogen, optionally administering booster doses thereof, and collecting the polyclonal antibodies from the animal.

3. Panel Tests

The marker proteins described herein can be used individually or in panels with one another or other additional markers for liver cancer such as described above, and including the marker alpha fetoprotein (upregulated in the blood of subjects afflicted with liver cancer). Where used in a panel test, the levels of the various markers are optionally but preferably tested from the same biological sample obtained from the subject (e.g., by detecting the quantities or amounts of various proteins in the same blood sample obtained from a patient). When combined in a panel test, the panel test may comprise determining an altered level for each of 2, 3 or 4 different proteins, up to 6, 8 or 10 or more different proteins (e.g., a panel of all proteins set forth in Tables 1-2 below). The combination of multiple marker proteins in a panel test serves to reduce the number of false positives and false negatives should an aberrant value for one particular member of the panel be found.

The present invention is explained in greater detail in the following non-limiting examples.

EXPERIMENTAL

Material and Methods

Tumor Tissues, Sera, and Cell Line. Tumor and non-tumor counterpart tissues were obtained from 7 patients with HCC. Following excision, the tissues were immediately frozen at −80° C. The tumoral or non-tumoral localizations of samples used for protein extraction were verified histologically. Histological analysis of non-tumor tissues showed that HCCs had developed on cirrhotic tissues. The tumors were classified histologically using the Edmondson grading system. All HCCs were defined as well or moderately differentiated. Sera were obtained from 27 healthy individuals, from 33 patients with chronic hepatitis, from 28 patients with cirrhosis, and from 34 patients with HCC, following informed consent. All patients were HCV-positive. The human hepatoma cell line PLC-PRF5 was cultured in Dulbecco's modified Eagle's medium supplemented with 10% fetal calf serum, 100 units/ml penicillin, and 100 units/ml streptomycin.

Two-Dimensional Polyacrylamide Gel Electrophoresis (2-D PAGE). Tumor and non-tumor tissues were solubilized in lysis buffer containing 9.5 M urea (Bio-Rad Laboratories, Hercules, Calif.), 2% Nonidet P-40, 2% carrier ampholytes, pH 4-8 (Gallard-Schlesinger Industries, Plainview, N.Y.), 2% β-mercaptoethanol, and 10 mM phenylmethanesulfonyl fluoride. Proteins (200 µg) were applied onto isofocusing gels. Isoelectric focusing was conducted using pH 4-8 carrier ampholytes. The first-dimension gel was loaded onto the second-dimension gel, after equilibration in 125 mM Tris, pH 6.8, 10% glycerol, 2% SDS, 1% dithiothreitol, and bromophenol blue. For the second-dimension separation, a gradient of 11 to 14% acrylamide (Serva; Crescent Chemical Company, Hauppauge, N.Y.) was used. Proteins were visualized by a photochemical silver-based staining technique.

Protein spot detection and quantitation. After the two-dimensional separation, each gel was scanned using a Kodak CCD camera. A 1,024×1,024 pixel format was used, yielding pixel widths of 163 µm, where each pixel had 256 possible gray-scale values (optical density). Spot detection was accomplished by Bio Image Visage System software (Bioimage, Ann Arbor, Mich.). The background-subtracted integrated intensity of each spot was obtained in Optical Density Units multiplied by $mm^2$. A set of 999 selected spots from each gel was matched to the spots on a master gel.[15] A total of 250 spots were chosen as ubiquitously expressed reference spots to allow adjustment for variation in protein loading and gel staining. Each of the 999 spots was then normalized in relation to the 10 closest neighboring reference spots.[16]

In-gel Enzymatic Digestion and Mass Spectrometry. Additional 2-D gels were silver-stained by successive incubations in 0.02% sodium thiosulfate for 2 min, 0.1% silver nitrate for 40 min, and 0.014% formaldehyde plus 2% sodium carbonate. The protein spots of interest were excised from the 2-D gels and destained for 10 min in 15 mM potassium ferricyanide and 50 mM sodium thiosulfate. Following three washes with water, the gel pieces were dehydrated in 100% acetonitrile for 5 min and dried for 20 min in a vacuum centrifuge. Digestion was performed by addition of 100 ng of trypsin (Promega Corporation, Madison, Wis.) in 200 mM ammonium bicarbonate. Following overnight enzymatic digestion at 37° C., the peptides were extracted twice with 10% acetonitrile/10% formic acid. After centrifugation in a vacuum centrifuge, 5% acetonitrile/0.1% formic acid was added to the peptides. Peptide mixtures were analyzed by nanoflow capillary liquid chromatography coupled with electrospray quadrupole time of flight tandem mass spectrometry (ESI/Q-TOF MS/MS) in the Q-Tof Micro™ mass spectrometer (Waters Corporation, Milford, Mass.). ESI/Q-TOF MS/MS tandem spectra were recorded in the automated MS to MS/MS switching mode, with an m/z-dependent set of collision offset values. Singly-to triply-charged ions were selected and fragmented, with argon used as the collision gas. The acquired spectra were processed and searched against a non-redundant SwissProt protein sequence database using the ProteinLynx global server (available from Waters Corporation, 34 Maple Street, Milford, Mass. 01757 (telephone 508 478-2000). The molecular weight (MW) and pI of identified proteins were calculated using Compute pI/Mw software tool from ExPASy (the Expert Protein Analysis System of the Swiss Institute of Bioinformatics (Biozentrum—University of Basel, Klingelbergstrasse 50-70, 4056 Basel, Switzerland).

2-D, 1-D and Dot Immunoblotting. Proteins separated by 2D-PAGE were transferred to PVDF membranes. Immunoblotting was then performed with antibodies against calreticulin, SPA-600 (StressGen Biotechnologies Corporation, Victoria, Canada) and T-19 (Santa Cruz Biotechnology), followed by incubation with horseradish peroxidase-conjugated anti-rabbit (Amersham Biosciences, Piscataway, N.J.) or anti-goat (Sigma-Aldrich, St. Louis, Mo.) IgG antibodies. Immunoreactivity was revealed by enhanced chemiluminescence using an ECL kit (Amersham Biosciences). For 1-D immunoblots, PLC-PRF5 cells were lysed in 20 mM Tris-HCl, pH 7.5, buffer containing 5 mM EDTA and 100 mM KCl. Proteins (50 µg) were loaded onto a 12% polyacrylamide gel, separated, and transferred onto nitrocellulose membrane (Amersham Biosciences). Immunoblotting was performed using a polyclonal anti-PDIA3 antibody (Stressgen Biotechnologies Corporation). Immunodetection was realized by ECL (Amersham Biosciences). For dot-immunoblot assays, PLC-PRF5 protein extracts (1-10 µg) and cell culture supernatant (5-25 µl) were blotted onto nitrocellulose membranes, using a dot-blot apparatus (Schleicher & Schuell, Keene, N.H.). The following antibodies were used: anti-calreticulin antibodies, PA3-900 (Affinity BioReagents, Golden, Colo.), N-19 (Santa Cruz Biotechnology), SPA-600 and SPA-601 (Stressgen Biotechnologies Corporation), anti-PDI antibodies, SPA-891 (Stressgen Biotechnologies Corporation), and H-160 (Santa Cruz Biotechnology), and anti-GRP78 antibodies N-20 and C-20 (Santa Cruz Biotechnology). Immunoreactivity was revealed by enhanced chemiluminescence using an ECL kit (Amersham Biosciences).

ELISA. Ninety six-well microplates (Nalge Nunc International, Rochester, N.Y.) were coated overnight with 0.5 µg/ml anti-calreticulin N-19 or 1 µg/ml anti-ERp57 N-20 antibodies (Santa Cruz Biotechnology), diluted in 0.05M carbonate-bicarbonate. After blocking with 1% BSA for 2 hours at room temperature, 50 µl of serum (diluted 1:10 with 0.67% BSA) or 50 µl of 0.67% BSA used as a negative control, were added. Following four washes with PBS/0.05% Tween20, 0.45 µg/ml anti-calreticulin SPA-601 or 1 µg/ml anti-Erp57 SPA-725 antibodies (Stressgen Biotechnologies Corporation) diluted in 0.67% BSA were added. Horseradish peroxidase-conjugated goat anti-mouse immunoglobulins (DakoCytomation California, Carpinteria, Calif.) (1:500 dilution in 0.67% BSA) followed by addition of 50 µl TMB one solution (Promega Corporation) were used for detection. The reaction was stopped by addition of IN sulfuric acid (Acros Organics, Morris Plains, N.J.) and the absorbance was measured at 450 nm using SpectraMax® Plus[384] spectrophotometer (Molecular Devices, Sunnyvale, Calif., USA).

Results

Protein Quantification. Liver tumor tissues and non-tumor counterpart regions isolated from 7 patients with HCC were analyzed by high-resolution 2-D PAGE. Nine hundred and ninety-nine protein spots were detected in 2-D gels that localized in the pI range of 4 to 8 and relative molecular mass of 10 to 150 kDa. Using computer-assisted analysis, each individual protein spot was quantified according to integrated intensity, allowing the comparison of protein spot intensities between tumor and non-tumor counterpart regions from the same patient. We selected protein spots that showed variation in at least 4 out of the 7 patients. Using this criterion, 47 protein spots were selected, corresponding to 16 up-regulated and 31 down-regulated spots (Table 1). The position of these protein spots on 2-D PAGE is shown in FIG. 1.

TABLE 1

Protein spots modified in HCC

| Up-regulated spots | Samples displaying change (n = 7) | Mean change | Down-regulated spots | Samples displaying change (n = 7) | Mean change |
|---|---|---|---|---|---|
| 26 | 4 | 2.8 | 14 | 5 | 5.2 |
| 75 | 5 | 2.5 | 36 | 4 | 2.2 |
| 77 | 5 | 2.0 | 37 | 5 | ~10.1 |
| 114 | 4 | ~26.8 | 86 | 5 | ~28.0 |
| 151 | 4 | 5.2 | 106 | 4 | 5.8 |
| 153 | 5 | 4.9 | 111 | 4 | 4.9 |
| 154 | 5 | 4.8 | 112 | 5 | 2.9 |
| 157 | 5 | 2.4 | 148 | 4 | ~67.0 |
| 240 | 4 | 3.5 | 150 | 4 | 4.9 |
| 307 | 5 | 6.3 | 175 | 5 | 4.4 |
| 353 | 4 | 4.0 | 255 | 5 | ~13.9 |
| 355 | 4 | 6.5 | 263 | 6 | 1.8 |
| 357 | 4 | 3.0 | 299 | 5 | ~26.3 |
| 500 | 5 | 7.2 | 300 | 4 | ~27.4 |
| 517 | 4 | 3.8 | 329 | 4 | 3.0 |
| 641 | 5 | 7.2 | 337 | 6 | 1.5 |
|  |  |  | 345 | 5 | ~41.0 |
|  |  |  | 346 | 5 | ~80.0 |
|  |  |  | 348 | 5 | ~14.8 |
|  |  |  | 366 | 4 | ~27.0 |
|  |  |  | 387 | 4 | 2.7 |
|  |  |  | 426 | 5 | ~33.0 |
|  |  |  | 428 | 5 | ~50.0 |
|  |  |  | 430 | 5 | ~33.0 |
|  |  |  | 438 | 4 | ~18.2 |
|  |  |  | 439 | 5 | ~52.0 |
|  |  |  | 453 | 4 | ~51.1 |
|  |  |  | 462 | 5 | ~75.0 |
|  |  |  | 473 | 6 | 1.7 |
|  |  |  | 486 | 5 | 7.8 |
|  |  |  | 502 | 5 | ~50.0 |

The ~ indicates fold change calculation for which the smaller value is replaced by an estimate of the minimum value for detectable signal.

Figure 2:
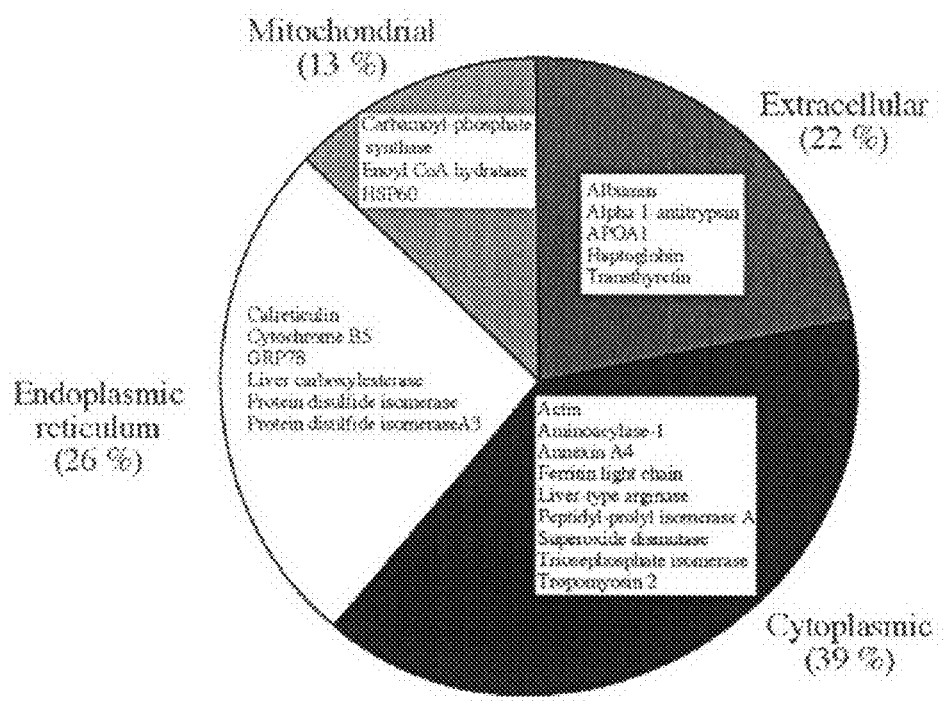
FIG. 2. Subcellular localization of identified proteins. The subcellular localization of the 23 unique proteins identified by ESI-QTOF-MS/MS is shown in the pie chart. Each individual protein was linked to a specific subcellular localization according to GO terms.

Protein Spot Identification. Of the 47 selected protein spots, 3 (spots 111, 112 and 150) had been previously identified by our group.[17] The remaining 44 protein spots were cut from additional 2-D PAGE gels and processed for mass spectrometry identification. Forty-one of these protein spots were identified unambiguously by ESI/Q-TOF MS/MS, while 2 protein identifications were obtained for spot 366, and no identification was obtained for spots 345 and 346. Protein spot identifications are presented in Table 2. Overall, the 45 protein spots identified corresponded to 23 distinct genes, belonging to 4 major sub-cellular groups: cytoplasmic proteins (39%), mitochondrial proteins (13%), extracellular proteins (22%), and components of the endoplasmic reticulum (ER) (26%) (FIG. 2).

TABLE 2

Protein spot identification

| Spot | Name | MS Identification (Peptide Matched) | Calculated MW/pI | Estimated MW/pI | Uni-gene | Swiss-prot |
|---|---|---|---|---|---|---|
| Up-regulated |  |  |  |  |  |  |
| 26 | HSP60 | 17 | 61/5.8 | 60/5.3 | Hs.79037 | P10809 |
| 75 | Albumin | 5 | 69/5.9 | 48/5.6 | Hs.184411 | P02768 |
| 77 | Albumin | 5 | 69/5.9 | 48/5.8 | Hs.184411 | P02768 |
| 114 | Tropomyosin 2 | 4 | 33/4.6 | 35/4.4 | Hs.300772 | P07951 |
| 151 | CRT32 (calreticulin fragment) | 6 | — | 32/3.3 | Hs.353170 | P27797 |
| 153 | Alpha-1-antitrypsin | 1 | 48/7.7 | 35/4.0 | Hs.297681 | P01009 |
| 154 | Alpha-1-antitrypsin | 1 | 48/7.7 | 33/4.2 | Hs.297681 | P01009 |
| 157 | Alpha-1-antitrypsin | 2 | 48/7.7 | 31/4.3 | Hs.297681 | P01009 |
| 240 | Annexin A4 | 2 | 36/5.8 | 30/5.7 | Hs.422986 | P09525 |
| 307 | Triosephosphate isomerase | 1 | 26/6.5 | 27/7.0 | Hs.83848 | P00938 |
| 353 | APOA1 | 9 | 31/5.7 | 26/5.0 | Hs.93194 | P02647 |
| 355 | APOA1 | — | 31/5.7 | 25/5.1 | Hs.93194 | P02647 |
| 357 | APOA1 | 13 | 31/5.7 | 26/5.2 | Hs.93194 | P02647 |
| 500 | Alpha-1-antitrypsin | 7 | 48/7.7 | 16/5.2 | Hs.297681 | P01009 |
| 517 | Transthyretin | 3 | 16/5.7 | 15/5.5 | Hs.427202 | P02766 |
| 641 | GRP78 (BIP) | 3 | 72/5.1 | 16/5.2 | Hs.75410 | P11021 |
| Down-regulated |  |  |  |  |  |  |
| 14 | Calreticulin precursor | 6 | 48/4.3 | 70/4.4 | Hs.353170 | P27797 |
| 36 | Calreticulin | 4 | 48/4.3 | 59/4.0 | Hs.353170 | P27797 |
| 37 | Calreticulin | 10 | 48/4.3 | 53/3.6 | Hs.353170 | P27797 |
| 86 | Haptoglobin | 3 | 45/6.5 | 45/5.2 | Hs.75990 | P00738 |
| 106 | Aminoacylase-1 | 4 | 46/5.8 | 40/5.8 | Hs.334707 | Q03154 |
| 111 | CRT32-C | Ref 15 | 48/4.3 | 36/3.5 | Hs.353170 | P27797 |
| 112 | CRT32-B | Ref 15 | 48/4.3 | 36/3.5 | Hs.353170 | P27797 |
| 148 | Liver-type arginase | 9 | 35/7.2 | 35/7.0 | Hs.332405 | P05089 |
| 150 | CRT32-A | Ref 15 | 48/4.3 | 35/3.4 | Hs.353170 | P27797 |
| 175 | Actin | 7 | 42/5.3 | 33/5.5 | Hs.426930 | P02570 |
| 255 | HSP60 | 3 | 61/5.8 | 30/4.5 | Hs.79037 | P10809 |
| 263 | Carbamoyl-phosphate synthase 1 | 2 | 165/6.7 | 30/5.5 | Hs.50966 | P31327 |

TABLE 2-continued

Protein spot identification

| Spot | Name | MS Identification (Peptide Matched) | Calculated MW/pI | Estimated MW/pI | Uni-gene | Swiss-prot |
|---|---|---|---|---|---|---|
| 299 | Protein disulfide isomerase A3 | 10 | 57/6.0 | 29/6.0 | Hs.13751 | P30101 |
| 300 | Enoyl-CoA hydratase | 6 | 31/8.5 | 29/6.0 | Hs.76394 | P30084 |
| 329 | Protein disulfide isomerase A3 | 13 | 57/6.0 | 29/5.8 | Hs.13751 | P30101 |
| 337 | Triosephosphate isomerase | 6 | 26/6.5 | 26/6.0 | Hs.83848 | P00938 |
| 348 | Protein disulfide isomerase | 6 | 57/4.8 | 25/4.4 | Hs.410578 | P07237 |
| 366 | Enoyl-CoA hydratase | 7 | 31/8.5 | 26/5.8 | Hs.76394 | P30084 |
|  | Triosephosphate isomerase | 2 | 26/6.5 | 26/5.8 | Hs.83848 | P00938 |
| 387 | Liver-type arginase | 1 | 35/7.2 | 23/4.3 | Hs.332405 | P05089 |
| 426 | Ferritin light chain | 3 | 20/5.7 | 22/5.3 | Hs.39574 | P02792 |
| 428 | Ferritin light chain | 1 | 20/5.7 | 22/5.4 | Hs.39574 | P02792 |
| 430 | Ferritin light chain | 3 | 20/5.7 | 21/5.5 | Hs.39574 | P02792 |
| 438 | Alpha-1-antitrypsin | 3 | 20/6.0 | 20/6.0 | Hs.297681 | P01009 |
|  | Liver carboxylesterase | 2 | 62/6.5 | 22/6.2 | Hs.76688 | P23141 |
| 453 | Carbamoyl-phosphate synthase 1 | 5 | 165/6.7 | 19/5.3 | Hs.50966 | P31327 |
| 462 | Superoxide dismutase [Cu-Zn] | 1 | 16/6.0 | 19/7.2 | Hs.75428 | P00441 |
| 473 | Superoxide dismutase [Cu-Zn] | 4 | 16/6.0 | 18/5.7 | Hs.75428 | P00441 |
| 486 | Cytochrome b5 | 4 | 15/4.9 | 16/4.4 | Hs.83834 | P00167 |
| 502 | Peptidyl-prolyl isomerase A | 3 | 18/8.2 | 16/5.8 | Hs.401787 | P05092 |

Correlation with Transcript Levels. In parallel with the proteomic analysis, we compared the gene expression profiles of HCC and adjacent non-tumor tissues using oligonucleotide microarrays. Expression levels of the transcripts corresponding to the 23 individual proteins were examined (Table 3). Positive correlations between transcript and protein level variations were observed for only 7 out of the 23 proteins. Levels of Hsp60 and GRP78 mRNAs and proteins were higher in the tumor tissues, while levels of aminoacylase-1, carbamoyl-phosphate synthase 1, cytochrome b5, enoyl-CoA hydratase, and haptoglobin mRNAs and proteins were lower in the tumor tissues. It is likely that post-transcriptional and post-translational alterations account for the discrepancies between mRNA and protein levels.

TABLE 3

Correlation between transcript and protein level variations. A positive correlation was observed for the genes listed in bold. Mean NT and T are expressed in Affymetrix intensity values. As criteria for determining significant differences in mean gene mRNA expression levels, two-sample t tests were done on log-transformed data.

| Gene Name | Mean NT | Mean T | Fold | p value |
|---|---|---|---|---|
| Actin | 19784 | 22515 | 1.14 | 0.530 |
| Albumin | 23641 | 11207 | −2.11 | 0.000 |
| Alpha-1-antitrypsin | 69290 | 62071 | −1.12 | 0.024 |
| Aminoacylase-1 | 10381 | 7675 | −1.35 | 0.007 |
| Annexin A4 | 4583 | 4782 | 1.04 | 0.545 |
| APOA1 | 60528 | 36653 | −1.65 | 0.018 |
| Calreticulin | 5580 | 6061 | 1.09 | 0.254 |
| Carbamoyl-phosphate synthase 1 | 22269 | 13772 | −1.62 | 0.008 |
| Cytochrome b5 | 21562 | 13869 | −1.55 | 0.004 |
| Enoyl-CoA hydratase | 15904 | 11123 | −1.43 | 0.011 |
| Ferritin light chain | 71534 | 78385 | 1.10 | 0.018 |
| GRP78 | 5581 | 7547 | 1.35 | 0.000 |
| Haptoglobin | 41446 | 25451 | −1.63 | 0.017 |
| Hsp60 | 17124 | 23105 | 1.35 | 0.000 |
| Liver carboxylesterase | 12887 | 15857 | 1.23 | 0.883 |
| Liver-type arginase | 10704 | 8231 | −1.30 | 0.088 |
| Peptidyl propyl isomerase | 24377 | 32685 | 1.34 | 0.026 |
| Protein disulfide isomerase | 32404 | 38211 | 1.18 | 0.003 |
| Protein disulfide isomerase A3 | 3370 | 4455 | 1.32 | 0.001 |
| Superoxide dismutase [Cu-Zn] | 18511 | 17217 | −1.08 | 0.257 |
| Transthyretin | 50195 | 39128 | −1.28 | 0.020 |
| Triosephosphate isomerase | 4164 | 5862 | 1.41 | 0.205 |
| Tropomyosin 2 | 373 | 563 | 1.51 | 0.127 |

Identification of Protein Cleavages in HCC. Protein separation by 2D-PAGE discriminates between post-translationally modified or processed protein isoforms. Twelve out of the 45 protein spots identified by mass spectrometry and listed in Table 2 had an apparent molecular weight significantly smaller than the predicted value for the corresponding intact protein, suggesting that these protein spots may correspond to protein fragments resulting from proteolytic cleavages. These 12 protein spots correspond to 7 distinct genes, including 5 that encode proteins of the ER: calreticulin, PDIA3, PDI, GRP78 and liver carboxylesterase. The other 2 proteins, Hsp60 and carbamoyl-phosphate synthase 1, are mainly mitochondrial, although partial localization in the ER has been reported for both proteins.

Figure 3:
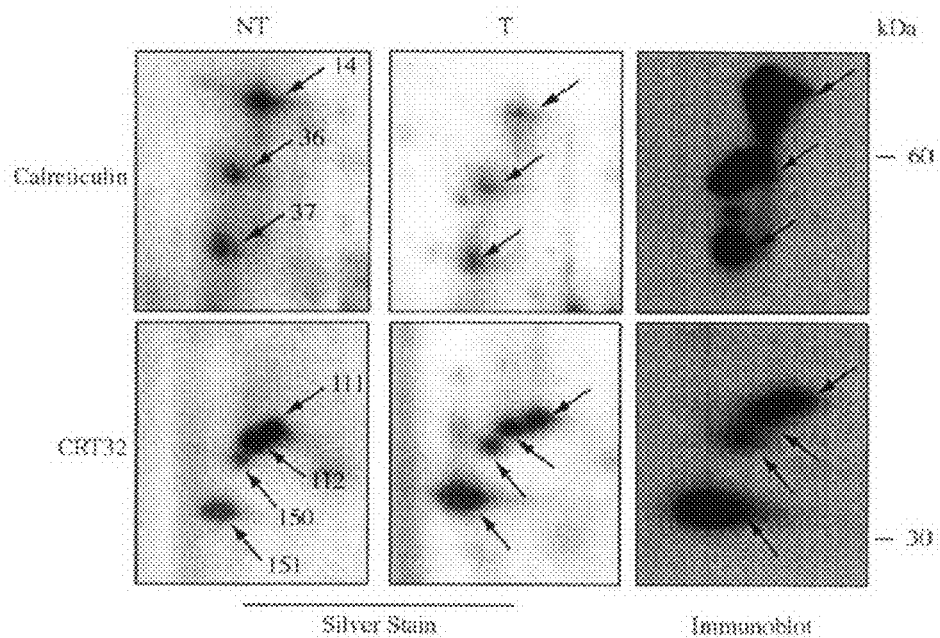
FIG. 3. 2-D pattern of calreticulin isoforms in tumor tissue. Close-up sections of 2-D gels from non-tumor (NT) and tumor (T) tissues are shown for the full-length calreticulin and CRT32. 2-D immunoblot analysis was also performed using a specific antibody directed against the C-terminal end of calreticulin (SPA-600).

Characterization of Calreticulin. The dysregulated proteins in HCC included the precursor and full-length calreticulin isoforms (spots 14, 36 and 37) which were reduced in HCC compared to non-tumor tissues. Concomitant with this down-regulation, an increase in another calreticulin form (Crt32, spot 151), with an estimated molecular mass of 32 kDa and pI of 4.1) was observed in the tumor tissues of the same patients (FIG. 3). Crt32 is a truncated form of calreticulin that we previously characterized in the hepatoma cell line PLC-PRF5, which corresponds to the C-terminal end of the protein (amino acids 157-400).[17] Identification of protein spots 14, 36, 37 and 151 as calreticulin isoforms was further confirmed by Western blot analysis, using an antibody directed against a C-terminal peptide of calreticulin (FIG. 3). Three additional spots (spots 111, 112 and 150) were also recognized by the antibody produced against the C-terminal region of calreticulin. These 3 calreticulin isoforms, which remain to be fully characterized, were reduced in HCC compared to non-tumor tissues. Taken together, these observations suggested that calreticulin is cleaved in HCC.

Figure 4:
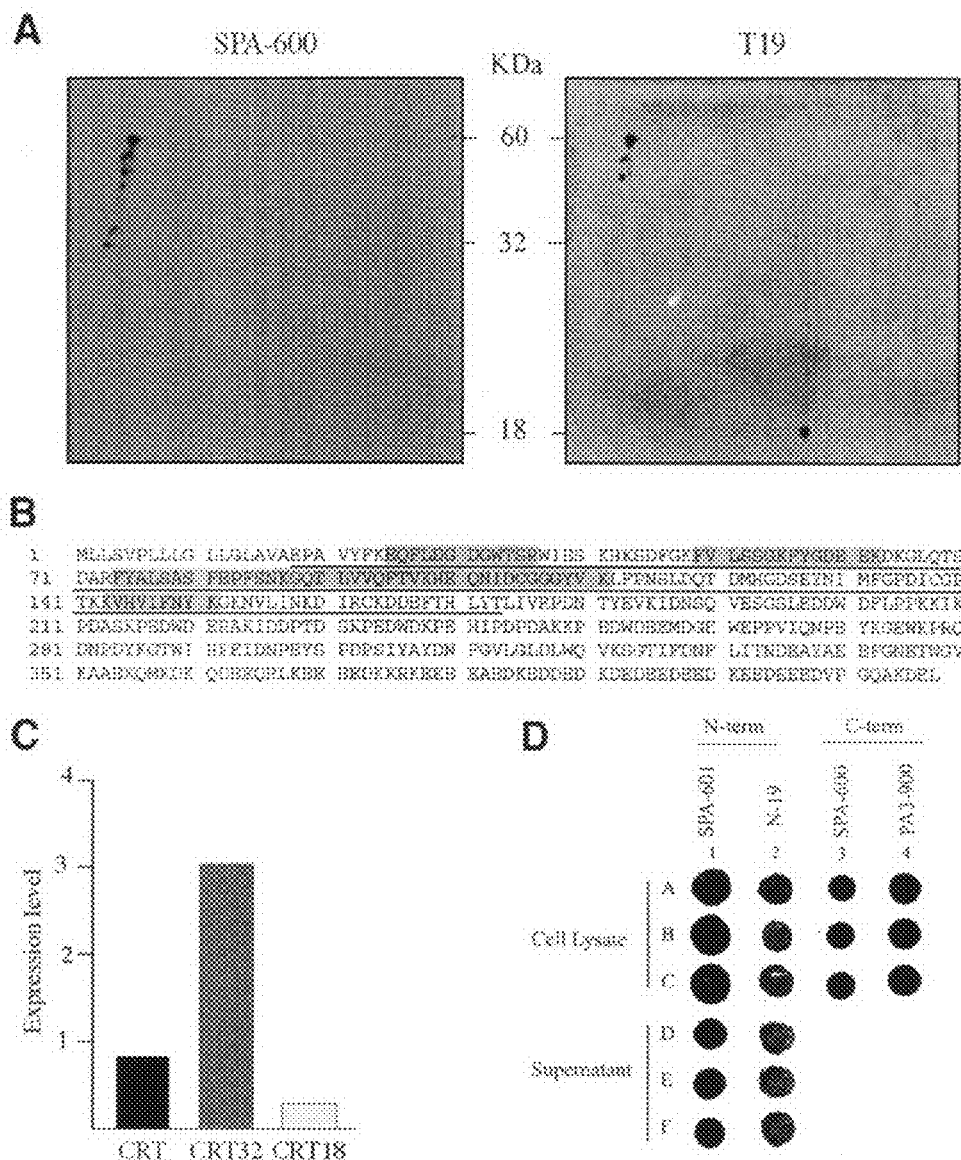
FIG. 4. Analysis of calreticulin isoforms. A, Immunoblot analysis of 2-D gels from tumor tissues performed with antibodies directed against the C-terminal end (SPA-600) or the N-terminal end (T19) of calreticulin. B, The underlined sequence of the full sequence shown (SEQ ID NO: 1) represents the expected sequence of CRT18. The dark boxes in the sequence (SEQ ID NO: 1) represent the peptides identified by mass spectrometry. C, After digitalization of silver stained 2-D gels, the integrated intensity of spots corresponding to the full length calreticulin, to CRT32, and to CRT18 in tumor tissues were measured. D. PLC-PRF5 cell lysate (A,B,C) and supernatant (D,E,F) were blotted onto a nitrocellulose membrane. Immunodetection was then performed using antibodies directed against the N-terminal end (SPA-601, N-19) or the C-terminal end (SPA-600, PA3-900) of calreticulin.

We sought to identify the N-terminal cleavage product of calreticulin in HCC. Two-dimensional Western blot experiments using the antibodies SPA-600 and T-19, directed against the C-terminal and N-terminal parts of calreticulin, respectively, were performed. A protein spot with estimated MW of 18 kDa and pI 6.5 reacted against the antibody T-19 but not against the antibody SPA-600, suggesting that it corresponds to an N-terminal fragment of calreticulin (FIG. 4A). Furthermore, the MW/pI estimated based on migration in 2-D gels were in agreement with the calculated MW/pI (19.5 kDa/5.7) of the N-terminal product that, together with Crt32, constitutes the complete calreticulin sequence. Identification of this protein spot as the N-terminal end of calreticulin was further confirmed by mass spectrometry. After tryptic digestion, 8 of the resulting peptides matched the calreticulin sequence in the N-terminal domain of the protein (FIG. 4B). We designated this N-terminal truncated form of calreticulin as Crt18.

In contrast with Crt32, the level of Crt18 was not significantly increased in HCC compared to non-tumor tissues. In addition, Crt18 intensity was significantly lower than Crt32 intensity in the HCC 2-D patterns (FIG. 4C). These observations suggested that Crt18 may be less stable than Crt32 or that Crt18 may be released in the extracellular compartment. To examine these possibilities, we used the PLC-PRF5 cell line, in which both Crt32 and Crt18 were detected by 2-D PAGE (data not shown). Using antibodies directed against the N-terminal end (antibodies SPA-601 and N-19) or the C-terminal end (antibodies SPA-600 and PA3-900) of calreticulin, we demonstrated that Crt18 but not Crt32 was detected in the culture supernatant of the PLC-PRF5 cells (FIG. 4D). Therefore, we conclude that calreticulin is cleaved in HCC, leading to the generation of Crt32 and Crt18 fragments and to the subsequent release of Crt18 into the extracellular compartments.

Figure 5:
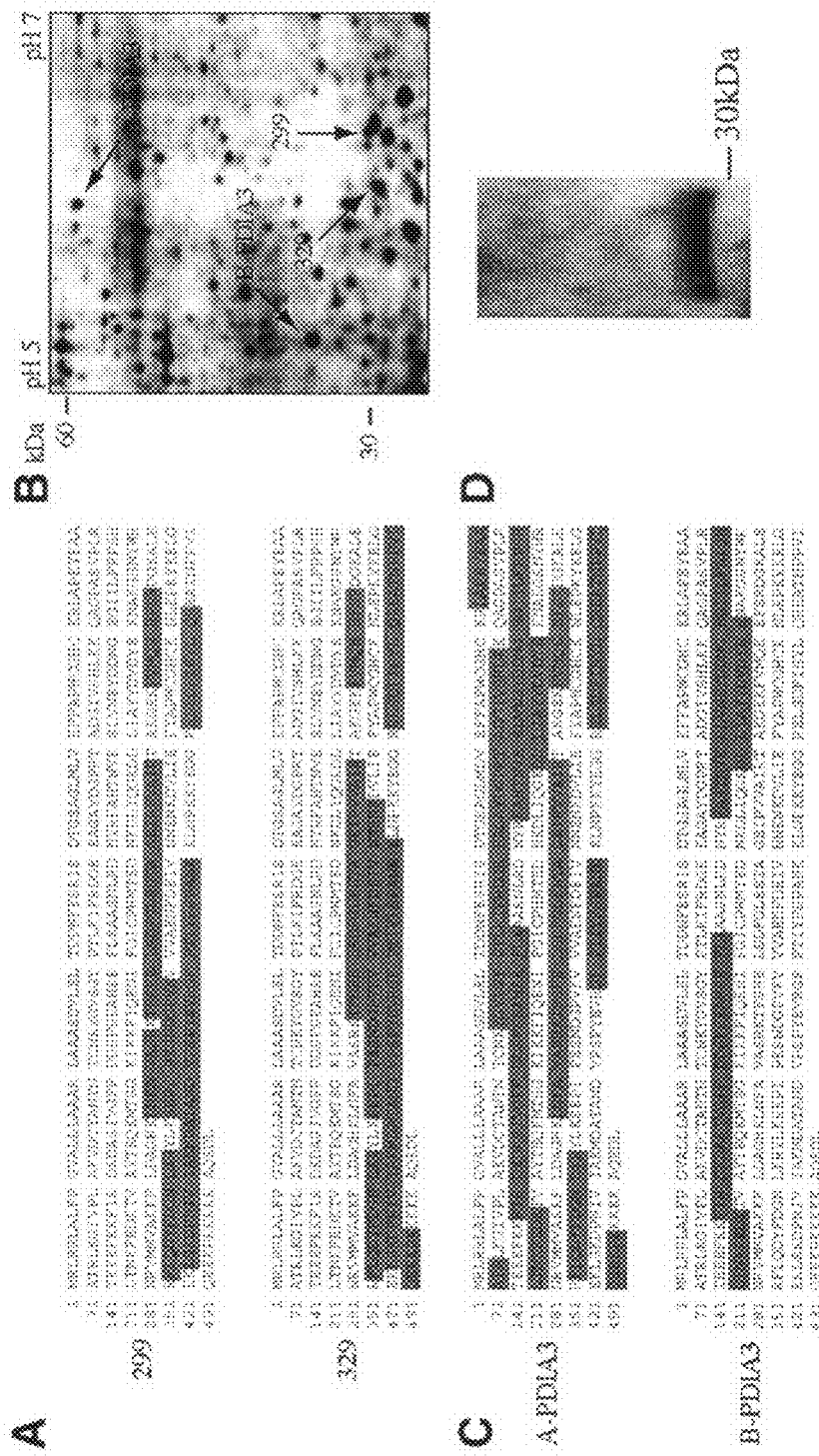
FIG. 5. Analysis of PDIA3 isoforms. A, The dark boxes in the two sequences (both SEQ ID NO: 2) represent the peptides identified by mass spectrometry for spots 299 and 329. B, 2-D silver-stained gel from liver tissue with the position of the full-length PDIA3 (A-PDIA3) and PDIA3 cleavage isoforms (B-PDIA3, 299, 329). C, The dark boxes in the two sequences (both also SEQ ID NO: 2) represent the peptides identified by mass spectrometry for spots A-PDIA3 and B-PDIA3. D, Immunoblot analysis of PDIA3 expression in PLC-PRF5 supernatant. Fifty microliters of cell culture supernatant from PLC-PRF5 were subjected to 1D-PAGE and immunodetection was performed with a polyclonal antibody directed against PDIA3 (SPA-585).

Characterization of Protein Disulfide Isomerase A3 (PDIA3). Spots 299 and 329, with apparent MW of 29 kDa and pI of 6 and 5.8, respectively, were down-regulated in tumor tissues as compared to non-tumor counterparts. After enzymatic digestion using trypsin and analysis of the resulting peptides by mass spectrometry, the peptides were consistent with those derived from protein disulfide isomerase A3 (PDIA3), a protein with a MW of 57 kDa and a pI of 6. The matched peptides clustered in the C-terminal region of the protein, suggesting that spots 299 and 329 correspond to C-terminal fragment products of PDIA3 (FIG. 5A).

As with calreticulin, we wished to characterize further the PDIA3 proteolytic processing occurring in HCC. In addition to spots 299 and 329, two other protein spots on the HCC 2-D gels (A-PDIA3 and B-PDIA3), were identified as PDIA3 isoforms (FIG. 5B). A-PDIA3 was identified as the full-length PDIA3 protein, based on a total of 17 matched peptides that covered 41% of the full-length sequence. Moreover, the matched peptides did not cluster in a specific region of PDIA3 (FIG. 5C). B-PDIA3 is a PDIA3 fragment containing aa148-aa273 (FIG. 5C). Because of the size of this fragment, B-PDIA3 corresponds most likely to a fragment of PDIA3, complementary to spots 229 or 329. While no specific modulation in intensity of the full-length A-PDIA3 protein was observed between tumor and non-tumor tissues, oligonucleotide microarray analysis indicated that the expression of the PDIA3 transcript was slightly (1.3 fold) but significantly (p=0.001) increased in tumor as compared to non-tumor tissues. Taken together, these observations suggested that PDIA3 is specifically cleaved in HCC, leading to the generation of two highly similar C-terminal fragments (spots 299 and 329) and one complementary N-terminal cleaved product (B-PDIA3).

As observed with calreticulin, the lack of correlation between the intensities of these three spots suggested that cleavage products of PDIA3 may be released in the extracellular compartment. This assumption was verified in the PLC-PRF5 cell line, in which an approximately 30 kDa band was detected in the culture supernatant by Western blot using an antibody against PDIA3 (FIG. 5D).

Figure 6:
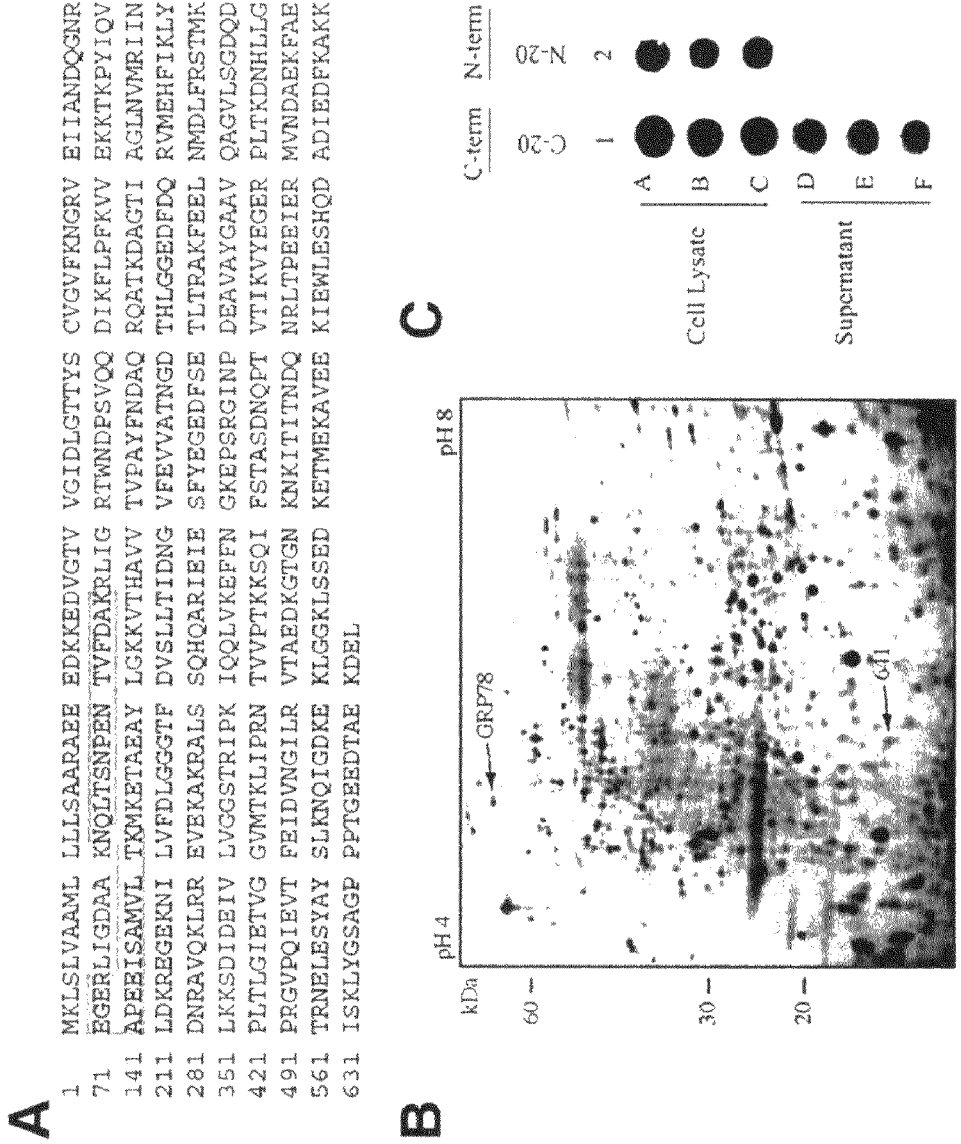
FIG. 6. Analysis of GRP78 isoforms. A, The dark boxes in the sequence (SEQ ID NO: 3) represent the peptides identified by mass spectrometry for spot 641. B, 2-D silver-stained gel from liver tissue with the position of the full-length GRP78 and GRP78 cleavage isoform 641. C, PLC-PRF5 cell lysate (A,B,C) and supernatant (D,E,F) were blotted onto a nitrocellulose membrane. Immunodetection was then performed using antibodies directed against the C-terminal end (C-20) or the N-terminal end (N-20) of GRP78.

Cleavage of Other ER Proteins and their Detection in the Extracellular Compartment. Another ER protein, GRP78, exhibited cleavage in HCC. Spot 641, a protein spot with an apparent molecular weight of 16 kDa, up-regulated in HCC, was identified by mass spectrometry as GRP78, a protein of 72 kDa. The peptides obtained by mass spectrometry from spot 641 matched the N-terminal end of the GRP78 sequence, suggesting that spot 641 corresponds to an N-terminal fragment of GRP78 (FIG. 6A). The full-length GRP78 protein was localized on the HCC 2-D patterns (FIG. 6B). No variation in intensity of the full-length protein was observed in tumor compared to non-tumor tissues. However, oligonucleotide microarray analysis indicated that the expression of the GRP78 transcript was slightly (1.35 fold) but significantly (p<0.001) increased in tumor as compared to non-tumor tissues. These observations suggested that GRP78 is cleaved in HCC. Using antibodies directed against the N-terminal end (N-20) or the C-terminal end (C-20) of GRP78, we detected a C-terminal fragment of GRP78 in the culture supernatant of PLC-PRF5 cells (FIG. 6C).

Figure 7:
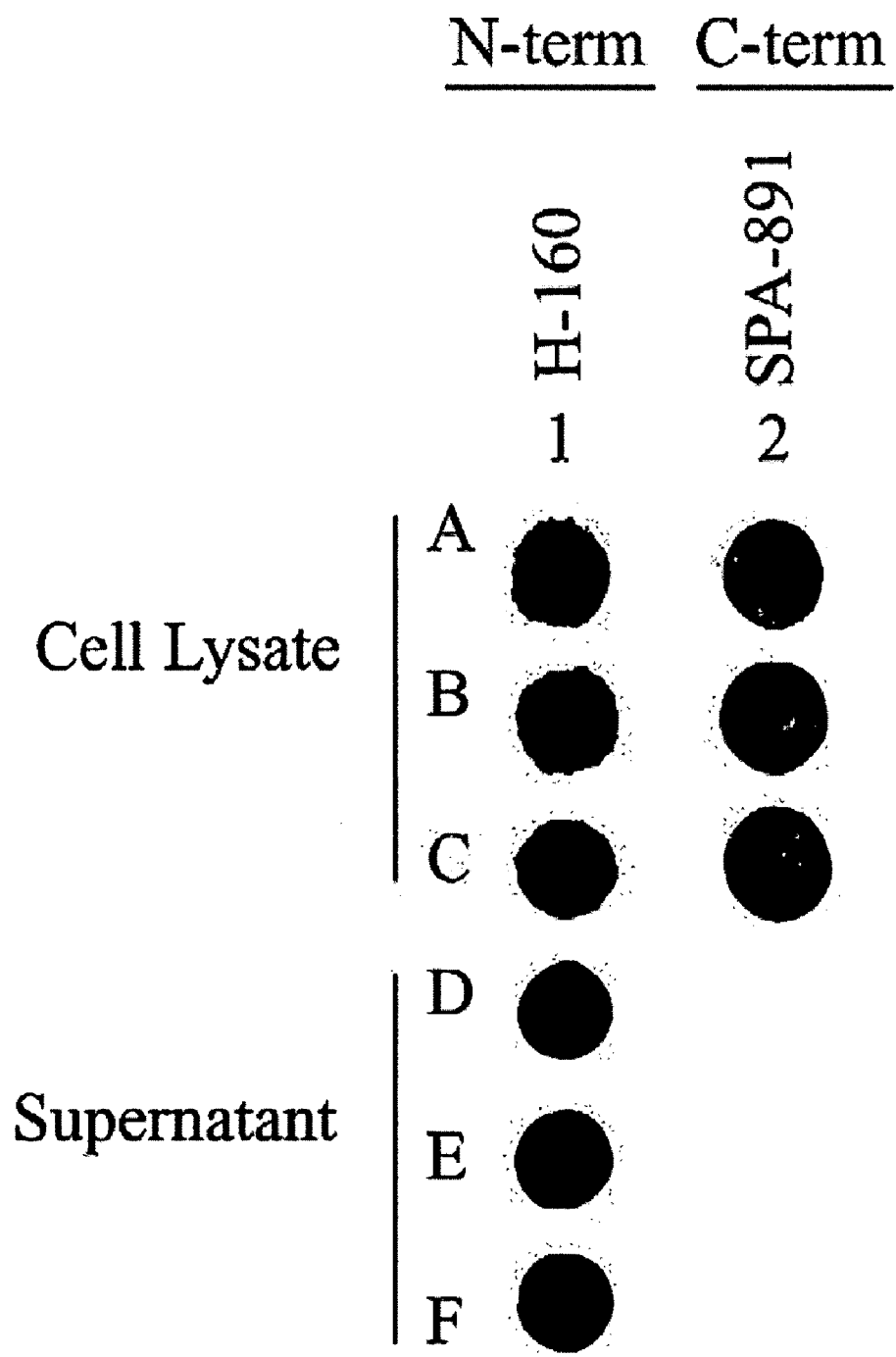
FIG. 7. Analysis of PDI isoform. PLC-PRF5 cell lysate (A,B,C) and supernatant (D,E,F) were blotted onto a nitrocellulose membrane. Immunodetection was then performed using antibodies directed against the N-terminal end (H-160) or the C-terminal end (SPA-891) of PDI.

Spot 348, with an apparent MW of 25 kDa was identified by ESI/Q-TOF MS/MS as protein disulfide isomerase (PDI), a protein of 57 kDa. All generated peptides matched with the N-terminal end of the protein, to a region spanning amino acids 79 to 230 (data not shown). Using antibodies directed against the N-terminal end (H-160) or the C-terminal end (SPA-891) of the protein, we detected an N-terminal fragment of PDI in the culture supernatant of PLC-PRF5 cells (FIG. 7).

Detection of Calreticulin and PDIA3 in Sera of HCC Patients. We investigated the possibility that calreticulin and PDIA3 cleavage fragments could be detected in serum of patients with HCC. We developed sandwich ELISAs using antibodies directed against the N-terminal end of calreticulin and antibodies directed against the N-terminal end of PDIA3. A statistically highly significant difference in Crt18 serum levels between patients with HCC (n=34) and healthy individuals (n=27) was observed (p=0.0002) (FIG. 8A). Similar data were obtained for the PDIA3 fragment. The difference in PDIA3 fragment serum levels between patients with HCC and healthy individuals was highly significant (p<0.0001)

Figure 8:
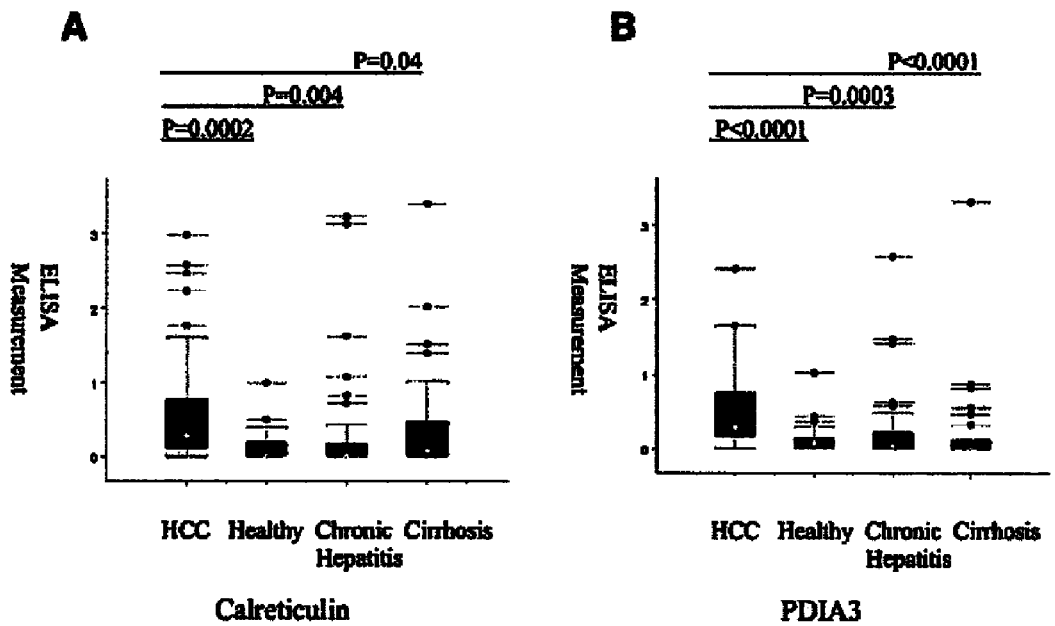
FIG. 8. Measurement by ELISA of calreticulin and PDIA3 fragments in sera. Levels of calreticulin (A) and PDIA3 (B) fragments were measured by ELISA in sera obtained from patients with HCC (n=34), patients with chronic hepatitis (n=33), patients with cirrhosis (n=28) and healthy individuals (n=27).

(FIG. 8B). We then investigated the possibility that Crt18 and PDIA3 fragments could be present in significantly different amounts in sera from patients with HCC and from patients at-risk of developing HCC, namely patients with chronic hepatitis and patients with cirrhosis. Levels of Crt18 and PDIA3 fragment were measured by ELISA in serum obtained from 33 patients with chronic hepatitis and 28 patients with cirrhosis. While Crt18 and PDIA3 fragment were detected at high levels in some patients in the high risk groups, amounts of both Crt18 and PDIA3 fragment were significantly different between patients with HCC and patients with chronic hepatitis (p=0.004 and p=0.0003 for Crt18 and PDIA3, respectively) or patients with cirrhosis (p=0.04 and p<0.0001 for Crt18 and PDIA3, respectively) (FIG. 8).

Figure 9:
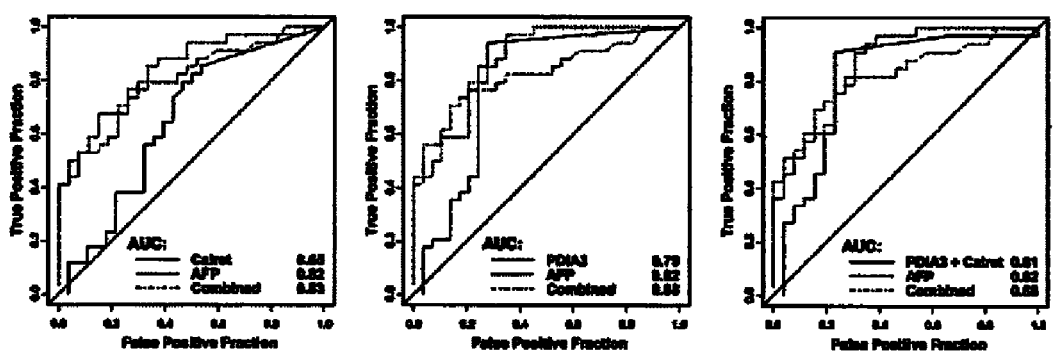
FIG. 9. ROC curves comparing calreticulin, PDIA3 and AFP individually or in combination in patients with HCC versus those with cirrhosis.

ROC curves were plotted to define the optimal cutoff values and to identify the sensitivity and specificity for serum calreticulin, PDIA3) and AFP in differentiating patients with HCC vs. those with cirrhosis (FIG. 9). Using 0.3 as pre-specified acceptable False Positive Fraction, sensitivity and specificity for calreticulin with an optimal cutoff point of 0.44 relative unit, were 58% and 71%, respectively; sensitivity and specificity for PDIA3 with an optimal cutoff point of 0.06 relative unit, were 94% and 72%, respectively; sensitivity and specificity of AFP with an optimal cutoff point of 11.7 ng/ml were 76% and 69%, respectively. At 20 ng/ml (recommended cutoff for AFP), sensitivity and specificity of AFP were 70% and 86%, respectively. Used alone, PDIA3 showed the greatest sensitivity (94%) in differentiating patients with HCC with those with cirrhosis. We then evaluated the sensitivity and specificity of calreticulin and PDIA3 combined and in combination with AFP. The best results were obtained by combining PDIA3 with AFP with 97% sensitivity (Table 4). Indeed, PDIA3 levels were elevated in all HCC patients with an AFP <20 ng/ml and in all HCC patients with an AFP <11.7 ng/ml (cutoff established by the ROC curve in this study).

TABLE 4

Calreticulin, PDIA3 and AFP, alone or in combination, for differentiation of patients with HCC from those with cirrhosis.

| Protein | Sensitivity | Specificity | Positive Pred. Value | Negative Pred. Value |
|---|---|---|---|---|
| AFP(>11.7 ng/ml) | 76 | 69 | 75 | 74 |
| AFP(>20 ng/ml) | 71 | 86 | 86 | 71 |
| Caireticulin (>0.44 relative unit) | 58 | 71 | 62 | 49 |
| PDIA3 (>0.059 relative unit) | 94 | 72 | 80 | 91 |
| Caireticulin + PDIA3 | 91 | 77 | 83 | 87 |
| Caireticulin + AFP | 79 | 70 | 77 | 73 |
| PDIA3 + AFP | 97 | 69 | 77 | 95 |
| Catreticulin + PDIA3 + AFP | 94 | 69 | 78 | 88 |

DISCUSSION

Most proteomic analyses of HCC tissues, including this study, have been performed using 2-D PAGE followed by MS. This technique has led to the identification of a large number of proteins modified in HCC compared to adjacent non-tumor tissues.[14] In agreement with these studies, we describe here a decrease in carbamoyl-phosphate synthase 1, cytochrome b5, liver-carboxylesterase, liver-type arginase, PDI, superoxide dismutase [Cu—Zn] and enoyl-CoA hydratase expression in tumor tissues compared to non-tumor counterparts.[18, 19] We also observed an increase in Hsp60, GRP78, triosephosphate isomerase, and ferritin light chain expression in HCC, as also previously reported.[18-21] Most proteins we identified are cytoplasmic. Other important groups include mitochondrial proteins, extracellular proteins and components of the ER. In the human proteome, the proportion of proteins assigned to the mitochondria and ER components is 4% and 3%, respectively.[22] Our findings therefore suggest that mitochondria- and ER-associated cellular functions may be specifically dysregulated in HCC. Protein separation by 2-D PAGE discriminates between post-translationally modified or processed protein isoforms. However, most studies reported to date have not presented any information regarding the specific protein isoforms, with the exception of the identification of specific protein alterations of aldehyde dehydrogenase[23] and aldose reductase-like protein[24] in HCC.

In our analysis, 27% of the protein spots we identified as modified in HCC corresponded to proteolytic cleavages as demonstrated by the smaller apparent Mw and the cluster of the peptides identified by MS within a specific region of the protein sequence. Interestingly, most of them corresponded to proteins expressed in the ER, including calreticulin, PDIA3, PDI, GRP78, and liver carboxylesterase. The ER is the site of synthesis and maturation of proteins destined for secretion, for the plasma membrane, and for the secretory and endocytic organelles. For glycoproteins, the ER possesses a dedicated maturation system, which assists folding and ensures the quality of final products before ER release. ER chaperones and folding enzymes such as GRP78, calreticulin, PDIA3, and PDI are not only responsible for assisting the folding and assembly process but also serve as retention anchors for immature proteins.[25] Calreticulin interacts with nascent and newly-synthesized glycoproteins in the ER and serves as a molecular chaperone during folding. Together with calnexin and PDIA3, calreticulin is responsible for quality control and folding in newly-synthesized glycoproteins.[26, 27] The amino acid sequence of PDIA3 is highly similar to that of PDI and these two proteins show strong analogies in function. GRP78 is a resident protein of the ER and is one of the most abundant ER chaperones. Many secretion incompetent proteins are found in stable association with GRP78 and are retained in the ER. Some proteins which are destined for secretion transiently associate with GRP78. The abundance of GRP78 and other ER chaperones influences the secretion efficiency of many proteins. Decrease in hepatic ER chaperone protein levels (GRP78, PDIA3, calreticulin) or in PDI activity leads to increased efficiency and amount of hepatic serum protein secretion.[28-31]

In addition, major histocompatibility complex (MHC) Class I maturation involves interactions with classical chaperones (e.g., GRP78), substrate-feature-specific chaperones (e.g., calreticulin), and catalyzing enzymes (e.g., PDIs), as well as with MHC class I dedicated accessory proteins (e.g., tapasin).[32] MHC class I down-regulation is a widespread mechanism used by tumor cells to escape destruction by anti-tumor cytotoxic T lymphocytes.[33, 34] Down-regulation of MHC class I antigen expression of tumors of different origins is frequently associated with the absence of or deficiencies in multiple components of the antigen presentation machinery.[35-41] Alterations in the expression of calreticulin, GRP78, PDI and PDIA3 in HCC may have important implications for MHC class I assembly, peptide loading, and presentation on the tumor cell surface and may be involved in the failure of the immune system to control HCC tumor progression.

Remarkably, following proteolytic cleavage, we demonstrated that fragments of calreticulin, GRP78, PDIA3 and PDI are released in the extracellular compartment. Furthermore, fragments of calreticulin and PDIA3 were detected at significantly higher levels in serum of patients with HCC compared to serum from healthy individuals, from patients with chronic hepatitis or patients with cirrhosis. We therefore identified HCC biomarkers with enough initial characterization to make them highly attractive as candidates for full validation studies.

We previously reported that in the serum of patients with HCC, circulating antibodies against calreticulin can be detected.[17] We can hypothesize that the presence of these autoantibodies is a consequence of the cleavage of calreticulin in HCC. Recently, cleavage of glycipan-3 and release of the $NH_2$-terminal fragment was also reported as specifically detected in the sera of patients with HCC.[42] A catalytic fragment of vitronectin was also recently proposed as a new serum marker of HCC in patients with chronic liver disease.[43] Specific isoforms in general and cleavage products in particular should therefore be further evaluated as new markers arising from protein processing specific for HCC.

REFERENCES

1. Bosch F X et al., *Gastroenterology* 2004; 127:S5-S16.
2. Llovet J M et al., *Lancet* 2003; 362:1907-1917.
3. El-Serag H B et al., *Hepatology* 2001; 33:62-65.
4. El-Serag H B. *Gastroenterology* 2004; 127:S27-34.
5. Bruix J, et al., *J Hepatol* 2001; 35:421-430.
6. Di Bisceglie A M et al., *Gastroenterology* 2004; 127:S104-107.
7. Daniele B et al., *Gastroenterology* 2004; 127:S108-112.
8. Hong W S et al., *J Korean Med Sci* 1991; 6:206-213.
9. Marrero J A et al., *Hepatology* 2003; 37:1114-1121.
10. Mita Y et al., *Cancer* 1998; 82:1643-1648.
11. Capurro M et al., *Gastroenterology* 2003; 125:89-97.
12. Yao D F et al., *Am J Clin Pathol* 1998; 110:743-749.
13. Cui R, et al., *Br J Cancer* 2003; 88:1878-1882.
14. Chignard N, Beretta L. *Gastroenterology* 2004; 127:S120-125.
15. Kuick R D et al., *Electrophoresis* 1991; 12:736-746.
16. Asakawa J et al., *Proc Natl Acad Sci USA* 1994; 91:9052-9056.
17. Le Naour F et al., *Mol Cell Proteomics* 2002; 1:197-203.
18. Kim W et al., *Clin Cancer Res* 2003; 9:5493-5500.
19. Lim S O et al., *Biochem Biophys Res Commun* 2002; 291:1031-1037.
20. Takashima M et al., *Proteomics* 2003; 3:2487-2493.
21. Park K S et al., *Hepatology* 2002; 35:1459-1466.
22. Anderson N L et al., *Mol Cell Proteomics* 2004; 3:311-326.
23. Park K S et al., *Int J Cancer* 2002; 97:261-265.
24. Zeindl-Eberhart E et al., *Hepatology* 2004; 39:540-549.
25. Kleizen B et al., *Curr Opin Cell Biol* 2004; 16:343-349.
26. Ellgaard L, Frickel E M. *Cell Biochem Biophys* 2003; 39:223-247.
27. Gelebart P et al., *Int J Biochem Cell Biol* 2005; 37:260-266.
28. Dhahbi J M et al., *Biochem Biophys Res Commun* 2001; 284:335-339.
29. Wang L et al., *J Biol Chem* 1997; 272:27644-27651.
30. Dorner A J et al., *Embo J* 1992; 11:1563-1571.
31. Dorner A J et al., *Mol Cell Biol* 1988; 8:4063-4070.
32. Paulsson K, Wang P. *Biochim Biophys Acta* 2003; 1641:1-12.
33. Mariricola F M et al., *Adv Immunol* 2000; 74:181-273.
34. Chang C C et al., *Curr Opin Immunol* 2004; 16:644-650.
35. Seliger B et al., *Immunol Today* 2000; 21:455-464.
36. Seliger B et al., *Clin Cancer Res* 2003; 9:1721-1727.
37. Seliger B et al., *Cancer Res* 2001; 61:8647-8650.
38. Seliger B et al., *Cancer Res* 2001; 61:1095-1099.
39. Garcia-Lora A et al., *Int J Cancer* 2003; 106:521-527.
40. Ogino T et al., *Clin Cancer Res* 2003; 9:4043-4051.
41. Dissemond J et al., *Cancer Lett* 2004; 203:225-231.
42. Hippo Y et al., *Cancer Res* 2004; 64:2418-2423.
43. Paradis V et al., *Hepatology* 2004; 41:40-47.

The foregoing is illustrative of the present invention, and is not to be construed as limiting thereof. The invention is defined by the following claims, with equivalents of the claims to be included therein.

That which is claimed is:

1. A method of screening for or diagnosing liver cancer in a subject, comprising:
   (a) collecting a blood or blood fraction sample from said subject; and then
   (b) detecting cleavage products of PDIA3 in said sample, cleavage of PDIA3 indicating said subject is afflicted with liver cancer.

2. The method of claim 1, wherein said blood sample comprises blood serum.

3. The method of claim 1 wherein said liver cancer is hepatocellular carcinoma.

4. The method of claim 1, wherein said cleavage is as compared to a control sample, with said control sample taken from the same or different subject.

5. The method of claim 1, wherein said subject is afflicted with chronic viral hepatitis, cirrhosis, or both.

6. The method of claim 1, wherein said detecting step is carried out by immunoassay.

7. The method of claim 1, further comprising the step of detecting an elevation of alpha fetoprotein in said sample, the presence of said elevation further indicating said subject is afflicted with liver cancer.

8. A method of screening for or diagnosing liver cancer in a subject, comprising:
   (a) collecting a blood or blood fraction sample from said subject; and then
   (b) detecting cleavage products of PDIA3 and an elevation of alpha fetoprotein in said sample;
   cleavage of PDIA3 and the presence of said elevation indicating said subject is afflicted with liver cancer.

9. The method of claim 8, wherein said blood sample comprises blood serum.

10. The method of claim 8, wherein said liver cancer is hepatocellular carcinoma.

11. The method of claim 8, wherein said cleavage is as compared to a control sample, with said control sample taken from the same or different subject.

12. The method of claim 8, wherein said subject is afflicted with chronic viral hepatitis, cirrhosis, or both.

13. The method of claim 8, wherein said detecting step is carried out by immunoassay.

14. A method of screening for or diagnosing liver cancer in a subject, comprising:
   (a) collecting a blood or blood fraction sample from said subject; and then
   (b) detecting a cleavage product of PDIA3 containing amino acid residues 148-273 in said sample;
   the cleaved PDIA3 product indicating said subject is afflicted with liver cancer.

15. The method of claim 14, wherein said blood sample comprises blood serum.

16. The method of claim 14, wherein said liver cancer is hepatocellular carcinoma.

17. The method of claim 14, wherein said cleavage is as compared to a control sample, with said control sample taken from the same or different subject.

18. The method of claim 14, wherein said subject is afflicted with chronic viral hepatitis, cirrhosis, or both.

19. The method of claim 14, wherein said detecting step is carried out by immunoassay, chromatography, or spectrometry.

20. The method of claim 14, further comprising the step of detecting an elevation of alpha fetoprotein in said sample, the presence of said elevation further indicating said subject is afflicted with liver cancer.

21. The method of claim 1, wherein said detecting step is carried out by chromatography.

22. The method of claim 1, wherein said detecting step is carried out by spectrometry.

23. The method of claim 8, wherein said detecting step is carried out by chromatography.

24. The method of claim 8, wherein said detecting step is carried out by spectrometry.

* * * * *

UNITED STATES PATENT AND TRADEMARK OFFICE
CERTIFICATE OF CORRECTION

PATENT NO. : 8,067,152 B2
APPLICATION NO. : 11/708202
DATED : November 29, 2011
INVENTOR(S) : Beretta It is certified that error appears in the above-identified patent and that said Letters Patent is hereby corrected as shown below:

In the Patent:

Column 8, Line 51: Please correct "addition of IN"
　　　　　　　　to read -- addition of 1N --

Column 11, Table 2, Headers Spot and Name: Please correct the Table entry
　　　　immediately after 438 by inserting -- 439 -- as shown below.
　　　　(Table headers are included for clarification)

| Spot | Name | MS Identification (Peptide Matched) | Calculated MW / pI | Estimated MW / pI | Uni-gene | Swiss-prot |
|---|---|---|---|---|---|---|
| 438 | Alpha-1-antitrypsin | 3 | 20 / 6.0 | 20 / 6.0 | Hs.297681 | P01009 |
| 439 | Liver carboxylesterase | 2 | 62 / 6.5 | 22 / 6.2 | Hs.76688 | P23141 |

Signed and Sealed this
Twenty-eighth Day of February, 2012

David J. Kappos
*Director of the United States Patent and Trademark Office*

SEQUENCE LISTING

```
<160> NUMBER OF SEQ ID NOS: 3

<210> SEQ ID NO 1
<211> LENGTH: 417
<212> TYPE: PRT
<213> ORGANISM: Homo sapiens
<220> FEATURE:
<221> NAME/KEY: MISC_FEATURE
<222> LOCATION: (18)..(173)
<223> OTHER INFORMATION: Sequence of CRT18

<400> SEQUENCE: 1

Met Leu Leu Ser Val Pro Leu Leu Gly Leu Leu Gly Leu Ala Val
1               5                   10                  15

Ala Glu Pro Ala Val Tyr Phe Lys Glu Gln Phe Leu Asp Gly Asp Gly
            20                  25                  30

Trp Thr Ser Arg Trp Ile Glu Ser Lys His Lys Ser Asp Phe Gly Lys
        35                  40                  45

Phe Val Leu Ser Ser Gly Lys Phe Tyr Gly Asp Glu Glu Lys Asp Lys
    50                  55                  60

Gly Leu Gln Thr Ser Gln Asp Ala Arg Phe Tyr Ala Leu Ser Ala Ser
```

```
            65                  70                  75                  80
        Phe Glu Pro Phe Ser Asn Lys Gly Gln Thr Leu Val Val Gln Phe Thr
                        85                  90                  95

Val Lys His Glu Gln Asn Ile Asp Cys Gly Gly Gly Tyr Val Lys Leu
                        100                 105                 110

Phe Pro Asn Ser Leu Asp Gln Thr Asp Met His Gly Asp Ser Glu Tyr
                        115                 120                 125

Asn Ile Met Phe Gly Pro Asp Ile Cys Gly Pro Gly Thr Lys Lys Val
                        130                 135                 140

His Val Ile Phe Asn Tyr Lys Gly Lys Asn Val Leu Ile Asn Lys Asp
        145                 150                 155                 160

Ile Arg Cys Lys Asp Asp Glu Phe Thr His Leu Tyr Thr Leu Ile Val
                        165                 170                 175

Arg Pro Asp Asn Thr Tyr Glu Val Lys Ile Asp Asn Ser Gln Val Glu
                        180                 185                 190

Ser Gly Ser Leu Glu Asp Asp Trp Asp Phe Leu Pro Pro Lys Lys Ile
                        195                 200                 205

Lys Asp Pro Asp Ala Ser Lys Pro Glu Asp Trp Asp Glu Arg Ala Lys
                        210                 215                 220

Ile Asp Asp Pro Thr Asp Ser Lys Pro Glu Asp Trp Asp Lys Pro Glu
        225                 230                 235                 240

His Ile Pro Asp Pro Asp Ala Lys Lys Pro Glu Asp Trp Asp Glu Glu
                        245                 250                 255

Met Asp Gly Glu Trp Glu Pro Pro Val Ile Gln Asn Pro Glu Tyr Lys
                        260                 265                 270

Gly Glu Trp Lys Pro Arg Gln Ile Asp Asn Pro Asp Tyr Lys Gly Thr
                        275                 280                 285

Trp Ile His Pro Glu Ile Asp Asn Pro Glu Tyr Ser Pro Asp Pro Ser
        290                 295                 300

Ile Tyr Ala Tyr Asp Asn Phe Gly Val Leu Gly Leu Asp Leu Trp Gln
        305                 310                 315                 320

Val Lys Ser Gly Thr Ile Phe Asp Asn Phe Leu Ile Thr Asn Asp Glu
                        325                 330                 335

Ala Tyr Ala Glu Glu Phe Gly Asn Glu Thr Trp Gly Val Thr Lys Ala
                        340                 345                 350

Ala Glu Lys Gln Met Lys Asp Lys Gln Asp Glu Glu Gln Arg Leu Lys
                        355                 360                 365

Glu Glu Glu Glu Asp Lys Lys Arg Lys Glu Glu Glu Ala Glu Asp
                        370                 375                 380

Lys Glu Asp Asp Glu Asp Lys Asp Glu Asp Glu Asp Glu Glu Asp
        385                 390                 395                 400

Lys Glu Glu Asp Glu Glu Asp Val Pro Gly Gln Ala Lys Asp Glu
                        405                 410                 415

Leu
```

<210> SEQ ID NO 2
<211> LENGTH: 505
<212> TYPE: PRT
<213> ORGANISM: Homo sapiens
<220> FEATURE:
<221> NAME/KEY: MISC_FEATURE
<222> LOCATION: (148)..(273)
<223> OTHER INFORMATION: Sequence of B-PDIA3

<400> SEQUENCE: 2

Met Arg Leu Arg Arg Leu Ala Leu Phe Pro Gly Val Ala Leu Leu Leu

-continued

```
  1               5              10              15
Ala Ala Ala Arg Leu Ala Ala Ala Ser Asp Val Leu Glu Leu Thr Asp
             20              25              30

Asp Asn Phe Glu Ser Arg Ile Ser Asp Thr Gly Ser Ala Gly Leu Met
             35              40              45

Leu Val Glu Phe Phe Ala Pro Trp Cys Gly His Cys Lys Arg Leu Ala
             50              55              60

Pro Glu Tyr Glu Ala Ala Ala Thr Arg Leu Lys Gly Ile Val Pro Leu
 65              70              75              80

Ala Lys Val Asp Cys Thr Ala Asn Thr Asn Thr Cys Asn Lys Tyr Gly
                 85              90              95

Val Ser Gly Tyr Pro Thr Leu Lys Ile Phe Arg Asp Gly Glu Glu Ala
            100             105             110

Gly Ala Tyr Asp Gly Pro Arg Thr Ala Asp Gly Ile Val Ser His Leu
            115             120             125

Lys Lys Gln Ala Gly Pro Ala Ser Val Pro Leu Arg Thr Glu Glu Glu
            130             135             140

Phe Lys Lys Phe Ile Ser Asp Lys Asp Ala Ser Ile Val Gly Phe Phe
145             150             155             160

Asp Asp Ser Phe Ser Glu Ala His Ser Glu Phe Leu Lys Ala Ala Ser
                165             170             175

Asn Leu Arg Asp Asn Tyr Arg Phe Ala His Thr Asn Val Glu Ser Leu
            180             185             190

Val Asn Glu Tyr Asp Asp Asn Gly Glu Gly Ile Ile Leu Phe Arg Pro
            195             200             205

Ser His Leu Thr Asn Lys Phe Glu Asp Lys Thr Val Ala Tyr Thr Glu
            210             215             220

Gln Lys Met Thr Ser Gly Lys Ile Lys Lys Phe Ile Gln Glu Asn Ile
225             230             235             240

Phe Gly Ile Cys Pro His Met Thr Glu Asp Asn Lys Asp Leu Ile Gln
                245             250             255

Gly Lys Asp Leu Leu Ile Ala Tyr Tyr Asp Val Asp Tyr Glu Lys Asn
            260             265             270

Ala Lys Gly Ser Asn Tyr Trp Arg Asn Arg Val Met Met Val Ala Lys
            275             280             285

Lys Phe Leu Asp Ala Gly His Lys Leu Asn Phe Ala Val Ala Ser Arg
            290             295             300

Lys Thr Phe Ser His Glu Leu Ser Asp Phe Gly Leu Glu Ser Thr Ala
305             310             315             320

Gly Glu Ile Pro Val Val Ala Ile Arg Thr Ala Lys Gly Glu Lys Phe
                325             330             335

Val Met Gln Glu Glu Phe Ser Arg Asp Gly Lys Ala Leu Glu Arg Phe
            340             345             350

Leu Gln Asp Tyr Phe Asp Gly Asn Leu Lys Arg Tyr Leu Lys Ser Glu
            355             360             365

Pro Ile Pro Glu Ser Asn Asp Gly Pro Val Lys Val Val Val Ala Glu
            370             375             380

Asn Phe Asp Glu Ile Val Asn Asn Glu Asn Lys Asp Val Leu Ile Glu
385             390             395             400

Phe Tyr Ala Pro Trp Cys Gly His Cys Lys Asn Leu Glu Pro Lys Tyr
                405             410             415

Lys Glu Leu Gly Glu Lys Leu Ser Lys Asp Pro Asn Ile Val Ile Ala
            420             425             430
```

-continued

```
Lys Met Asp Ala Thr Ala Asn Asp Val Pro Ser Pro Tyr Glu Val Arg
        435                 440                 445

Gly Phe Pro Thr Ile Tyr Phe Ser Pro Ala Asn Lys Lys Leu Asn Pro
    450                 455                 460

Lys Lys Tyr Glu Gly Gly Arg Glu Leu Ser Asp Phe Ile Ser Tyr Leu
465                 470                 475                 480

Gln Arg Glu Ala Thr Asn Pro Pro Val Ile Gln Glu Glu Lys Pro Lys
                485                 490                 495

Lys Lys Lys Lys Ala Gln Glu Asp Leu
                500                 505

<210> SEQ ID NO 3
<211> LENGTH: 654
<212> TYPE: PRT
<213> ORGANISM: Homo sapiens

<400> SEQUENCE: 3

Met Lys Leu Ser Leu Val Ala Ala Met Leu Leu Leu Ser Ala Ala
1               5                   10                  15

Arg Ala Glu Glu Glu Asp Lys Lys Glu Asp Val Gly Thr Val Val Gly
                20                  25                  30

Ile Asp Leu Gly Thr Thr Tyr Ser Cys Val Gly Val Phe Lys Asn Gly
            35                  40                  45

Arg Val Glu Ile Ile Ala Asn Asp Gln Gly Asn Arg Ile Thr Pro Ser
    50                  55                  60

Tyr Val Ala Phe Thr Pro Glu Gly Glu Arg Leu Ile Gly Asp Ala Ala
65                  70                  75                  80

Lys Asn Gln Leu Thr Ser Asn Pro Glu Asn Thr Val Phe Asp Ala Lys
                85                  90                  95

Arg Leu Ile Gly Arg Thr Trp Asn Asp Pro Ser Val Gln Gln Asp Ile
            100                 105                 110

Lys Phe Leu Pro Phe Lys Val Val Glu Lys Lys Thr Lys Pro Tyr Ile
    115                 120                 125

Gln Val Asp Ile Gly Gly Gly Gln Thr Lys Thr Phe Ala Pro Glu Glu
130                 135                 140

Ile Ser Ala Met Val Leu Thr Lys Met Lys Glu Thr Ala Glu Ala Tyr
145                 150                 155                 160

Leu Gly Lys Lys Val Thr His Ala Val Val Thr Val Pro Ala Tyr Phe
                165                 170                 175

Asn Asp Ala Gln Arg Gln Ala Thr Lys Asp Ala Gly Thr Ile Ala Gly
            180                 185                 190

Leu Asn Val Met Arg Ile Ile Asn Glu Pro Thr Ala Ala Ala Ile Ala
    195                 200                 205

Tyr Gly Leu Asp Lys Arg Glu Gly Glu Lys Asn Ile Leu Val Phe Asp
210                 215                 220

Leu Gly Gly Gly Thr Phe Asp Val Ser Leu Leu Thr Ile Asp Asn Gly
225                 230                 235                 240

Val Phe Glu Val Val Ala Thr Asn Gly Asp Thr His Leu Gly Gly Glu
                245                 250                 255

Asp Phe Asp Gln Arg Val Met Glu His Phe Ile Lys Leu Tyr Lys Lys
            260                 265                 270

Lys Thr Gly Lys Asp Val Arg Lys Asp Asn Arg Ala Val Gln Lys Leu
    275                 280                 285

Arg Arg Glu Val Glu Lys Ala Lys Arg Ala Leu Ser Ser Gln His Gln
290                 295                 300
```

-continued

```
Ala Arg Ile Glu Ile Glu Ser Phe Tyr Glu Gly Glu Asp Phe Ser Glu
305                 310                 315                 320

Thr Leu Thr Arg Ala Lys Phe Glu Glu Leu Asn Met Asp Leu Phe Arg
            325                 330                 335

Ser Thr Met Lys Pro Val Gln Lys Val Leu Glu Asp Ser Asp Leu Lys
        340                 345                 350

Lys Ser Asp Ile Asp Glu Ile Val Leu Val Gly Gly Ser Thr Arg Ile
    355                 360                 365

Pro Lys Ile Gln Gln Leu Val Lys Glu Phe Phe Asn Gly Lys Glu Pro
370                 375                 380

Ser Arg Gly Ile Asn Pro Asp Glu Ala Val Ala Tyr Gly Ala Ala Val
385                 390                 395                 400

Gln Ala Gly Val Leu Ser Gly Asp Gln Asp Thr Gly Asp Leu Val Leu
            405                 410                 415

Leu Asp Val Cys Pro Leu Thr Leu Gly Ile Glu Thr Val Gly Gly Val
        420                 425                 430

Met Thr Lys Leu Ile Pro Arg Asn Thr Val Val Pro Thr Lys Lys Ser
    435                 440                 445

Gln Ile Phe Ser Thr Ala Ser Asp Asn Gln Pro Thr Val Thr Ile Lys
450                 455                 460

Val Tyr Glu Gly Glu Arg Pro Leu Thr Lys Asp Asn His Leu Leu Gly
465                 470                 475                 480

Thr Phe Asp Leu Thr Gly Ile Pro Pro Ala Pro Arg Gly Val Pro Gln
            485                 490                 495

Ile Glu Val Thr Phe Glu Ile Asp Val Asn Gly Ile Leu Arg Val Thr
        500                 505                 510

Ala Glu Asp Lys Gly Thr Gly Asn Lys Asn Lys Ile Thr Ile Thr Asn
    515                 520                 525

Asp Gln Asn Arg Leu Thr Pro Glu Glu Ile Glu Arg Met Val Asn Asp
530                 535                 540

Ala Glu Lys Phe Ala Glu Asp Lys Lys Leu Lys Glu Arg Ile Asp
545                 550                 555                 560

Thr Arg Asn Glu Leu Glu Ser Tyr Ala Tyr Ser Leu Lys Asn Gln Ile
            565                 570                 575

Gly Asp Lys Glu Lys Leu Gly Gly Lys Leu Ser Ser Glu Asp Lys Glu
        580                 585                 590

Thr Met Glu Lys Ala Val Glu Glu Lys Ile Glu Trp Leu Glu Ser His
    595                 600                 605

Gln Asp Ala Asp Ile Glu Asp Phe Lys Ala Lys Lys Lys Glu Leu Glu
610                 615                 620

Glu Ile Val Gln Pro Ile Ile Ser Lys Leu Tyr Gly Ser Ala Gly Pro
625                 630                 635                 640

Pro Pro Thr Gly Glu Glu Asp Thr Ala Glu Lys Asp Glu Leu
            645                 650
```